(12) United States Patent
Saubers

(10) Patent No.: US 8,545,219 B2
(45) Date of Patent: *Oct. 1, 2013

(54) OUTIE TOOL FOR REMOVAL OF A PLASTIC TOOTH POSITIONING APPLIANCE OR ALIGNER (INVISIBLE BRACES) FROM TEETH OF A PATIENT

(75) Inventor: Nadine Marie Saubers, Chula Vista, CA (US)

(73) Assignee: Nadine Marie Saubers, Chula Vista, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/288,509

(22) Filed: Nov. 3, 2011

(65) Prior Publication Data

US 2012/0100499 A1   Apr. 26, 2012

Related U.S. Application Data

(63) Continuation of application No. 12/383,716, filed on Mar. 26, 2009, now Pat. No. 8,062,030.

(60) Provisional application No. 61/043,443, filed on Apr. 9, 2008.

(51) Int. Cl.
*A61C 7/02* (2006.01)
*A61C 3/00* (2006.01)

(52) U.S. Cl.
USPC .............................................. 433/3; 433/141

(58) Field of Classification Search
USPC ................ 433/1–4, 141, 143, 144, 145, 148, 433/229; 132/73, 321, 329; D24/135, 152; 7/166, 169, 170; 112/169; 72/458; 30/123.5, 30/123.7, 172, 279.2, 279.6, 287, 288, 294, 30/299, 304, 305, 314, 315, 316, 317; 254/25–27; 81/45; D28/64, 65, 91.2; 115/105.5; 157/1.3; 172/375; 600/184–246; D8/89

See application file for complete search history.

(56) References Cited

U.S. PATENT DOCUMENTS

| | | | | |
|---|---|---|---|---|
| 567,589 | A * | 9/1896 | Fredricks | 433/144 |
| 1,741,801 | A * | 12/1929 | White | 157/1.1 |
| 1,879,583 | A * | 9/1932 | Stowell | 72/458 |
| 2,121,129 | A * | 6/1938 | Malone | 474/130 |
| 2,457,231 | A * | 12/1948 | Henderson | 254/25 |
| 5,394,729 | A * | 3/1995 | Eisenhower, Jr. | 72/450 |
| 5,520,611 | A * | 5/1996 | Rao et al. | 600/245 |
| D568,124 | S * | 5/2008 | Stevens, Sr. | D8/14 |
| 2004/0226660 | A1* | 11/2004 | Kliskey | 157/1.3 |
| 2007/0072142 | A1* | 3/2007 | Staines et al. | 433/3 |
| 2008/0099737 | A1* | 5/2008 | Harpell | 254/25 |
| 2008/0160473 | A1* | 7/2008 | Li et al. | 433/3 |
| 2009/0246732 | A1* | 10/2009 | Creasman et al. | 433/141 |

\* cited by examiner

*Primary Examiner* — Todd Manahan
*Assistant Examiner* — Michael R Ballinger
(74) *Attorney, Agent, or Firm* — John L. Rogitz

(57) ABSTRACT

An apparatus and method for the efficient, safe, and hygienic removing of removable tooth positioning appliances such as aligners or other dental appliances from the teeth of a patient. A straight rigid barrel has a lever appendage on the proximal end for fully engaging and removing a lower aligner and a hook appendage on the distal end for fully engaging and removing an upper aligner.

11 Claims, 3 Drawing Sheets

OUTIE TOOL FOR REMOVAL OF A PLASTIC TOOTH POSITIONING APPLIANCE OR ALIGNER (INVISIBLE BRACES) FROM TEETH OF A PATIENT

CROSS-REFERENCE TO RELATED APPLICATIONS

This application is entitled to the benefit of Provisional Patent Application Ser. No.
APPLICATION NUMBER: U.S. 61/043,443
FILING DATE: Apr. 9, 2008

BACKGROUND OF THE INVENTION

Removable tooth positioning appliances (invisible braces), such as clear plastic aligners and retainers that tightly fit over teeth are commonly used in orthodontic treatments as an alternative to braces and other bonded orthodontic equipment for controlled tooth movement to a pre-determined position. These clear plastic tooth positioning appliances are not bonded to the teeth which they are used to manipulate but are made to be removed in order to eat, drink, brush, and floss the teeth as well as during dental procedures. The appliance is fabricated from a mold of the patient's teeth in order to provide accuracy of placement in compliance with the exact shape of the teeth or the exact shape and any necessary attachment devices. See U.S. Pat. No. 6,183,248 for an example of such a removable tooth positioning appliance which is incorporated herein in its entirety by reference. Total treatment time with clear plastic aligners averages 9-15 months and the average number of aligners worn during treatment is between 18 and 30, but both will vary from case to case. When teeth are moved into their final position patients are then only required to wear the aligners at night.

Removable tooth positioning appliances consist of a thin shell of clear material that conforms to a patient's teeth but just slightly out of alignment with the initial tooth configuration. By properly choosing the configuration, placement of the appliance over the teeth will move individual teeth to desired intermediate or final positions over time. These positioning appliances can be designed to fit over any number of teeth, and are typically designed to be placed over the entire top and/or bottom set of teeth.

To achieve the repositioning forces required to move a tooth from one position to another position these tooth positioning appliance must be relatively stiff (i.e. possess a high strength or high modulus) to provide a sufficient grip on the teeth. The stiffness provides the repositioning force necessary to move the teeth and ensures that the dental appliance remains firmly in position on the patient's teeth. The stiffness also permits the positioning appliance to grab hold of an anchor device or attachments on the tooth to apply a directed force to execute orthodontic tooth movements.

The stiffness of the tooth positioning appliance and the requirement that the appliance tightly conform to the teeth of the patient makes it difficult to remove these appliances. It is necessary to remove the positioning appliance many times daily in the course of the patient's daily life for cleaning, dental hygiene, to eat, and removal for cosmetic purposes and replacement in the course of treatment. Patients are instructed to use their fingers and fingernails to remove the appliances but they often find removing the appliances to be difficult and in many cases painful. Patients also find it unsanitary to be continually putting their hands in their mouths. Because removal of the appliances requires a lever action patients often will attempt to use household instruments, such as forks, spoons, or nut picks to remove their tooth positioning appliance. Using improvised instruments can damage the patient's teeth, gums and the appliance itself. During visits to the dental practitioner these practitioners use orthodontic instruments designed for other uses to remove the appliance. These orthodontic appliances often present the same problems and dangers as the patient's improvised instruments. For these reasons, it is desirable to provide a lightweight and convenient tool that is specifically designed to remove such tooth positioning appliances from a patient's teeth in a safe, easy, and effective manner.

BRIEF SUMMARY OF THE INVENTION

The OUTIE TOOL is designed to be used by people without any special training to remove their invisible braces. The OUTIE TOOL is light and compact, it is easy to carry in pocket or purse, it is easy and safe to use. The Outie Tool is a small piece of plastic (polypropylene food grade) with a short flat hook appendage on distal end and a flat lever appendage on the proximal end. The OUTIE TOOL is 11.5 cm long and 8 mm wide on each side. Each appendage, both hook and lever is sufficiently thin enough (1.5 mm) to easily fit under the appliance, in between the teeth. The person wearing the clear aligners inserts the lever appendage under the appliance that is covering the lower teeth and exerts a small amount of force upward in order to push the bottom aligner off The person inserts the hook appendage under the appliance that is covering the upper teeth and exerts a small amount of force downward to easily and safely pull the upper appliance off There are no dangers to the gums, teeth, or appliance in using the OUTIE TOOL when used as instructed. The OUTIE TOOL provides easy and safe removal in a hygienic manner. The OUTIE TOOL can be used by both dental practitioners and patients wearing invisible braces with no special training.

DETAILED DESCRIPTION OF THE INVENTION

The invention is called the OUTIE TOOL. The Outie Tool is manufactured by injection molding. A mold is created from the 3D design and precision-machined to form the features of the design illustrated, the barrel, hook appendage, and lever appendages. The molds are made from metal, usually either steel or aluminum. The material used is polypropylene food grade (PP) which is completely safe for food and medical usage; it is sufficiently hard and strong enough to withstand normal use without breaking or cracking. The material is fed into a heated barrel, mixed, and forced into a mold cavity where it cools and hardens to the configuration of the mold cavity.

Figure 1:
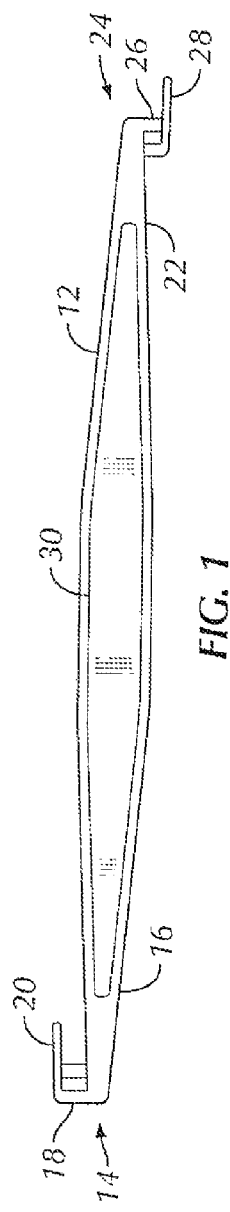
FIG. 1: Side View of OUTIE TOOL
Dimensions: Barrel length from side to side 11.5 cm, width in middle of barrel (up and down) 8 mm on all 4 sides

The Outie Tool solves all of the above problems as described below:

Referring now to FIG. 1 Side View of OUTIE TOOL is illustrative of the compact and lightweight design, easy and convenient for persons to carry them in purse or pocket during daily life. The straight, rigid design of the barrel is necessary to sufficiently grasp while applying mechanical force to remove the appliance. The barrel has to be straight in order to supply leverage.

Figure 2:
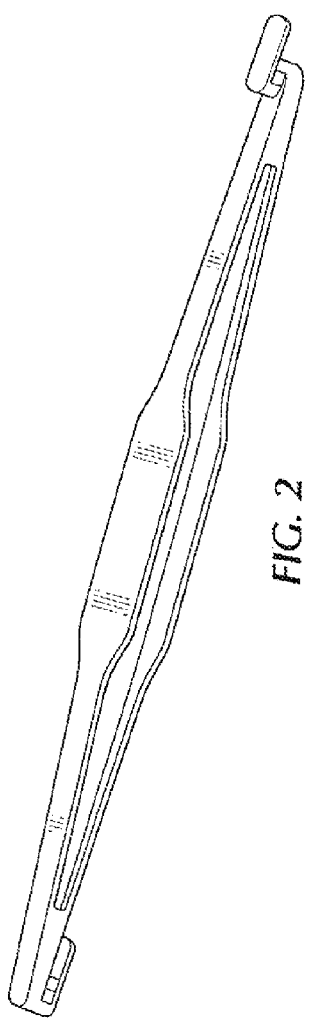
FIG. 2: Top View of OUTIE TOOL Hook appendage on left, lever appendage on right
Figure 3:
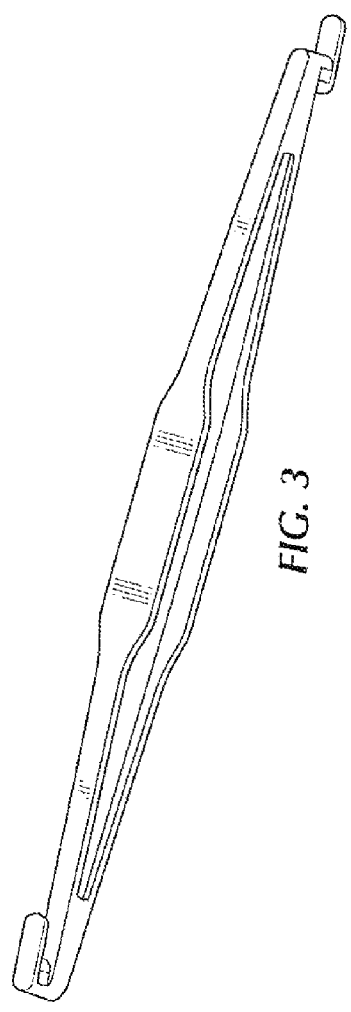
FIG. 3: Bottom View
Hook appendage on left, lever appendage on right
Figure 4:
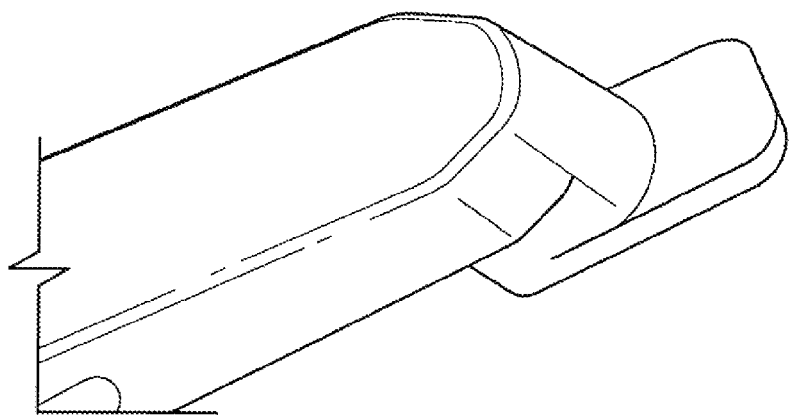
FIG. 4: Lever Appendage Close-up view
Lever Appendage pushes off bottom appliance from lower teeth
Figure 5:
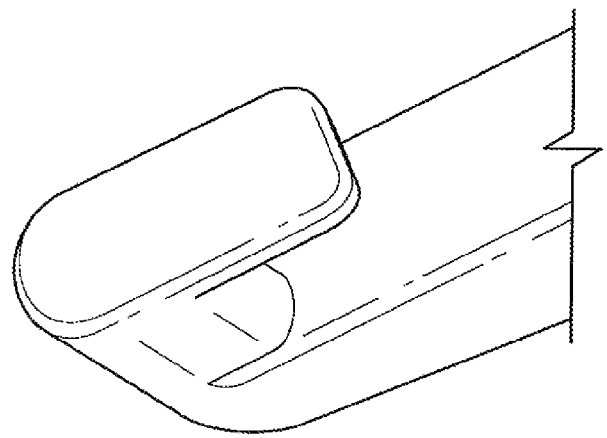
FIG. 5: Hook Appendage Close-up view
Hook appendage pulls off top appliance from upper teeth
Figure 8:
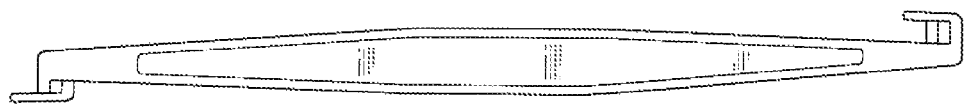
FIG. 8: Photo of actual OUTIE Tools

Referring now to FIG. 2 and FIG. 3 show the Hook appendage on left, and the Lever appendage on right. The Hook appendage and Lever appendage are 7 mm long, 3 mm wide and 1.5 mm thick. These dimensions make it easy to slide the appendage in between the appliances and the teeth, engage fully, and remove the aligners with minimal force while being completely safe.

Figures 6, 7:
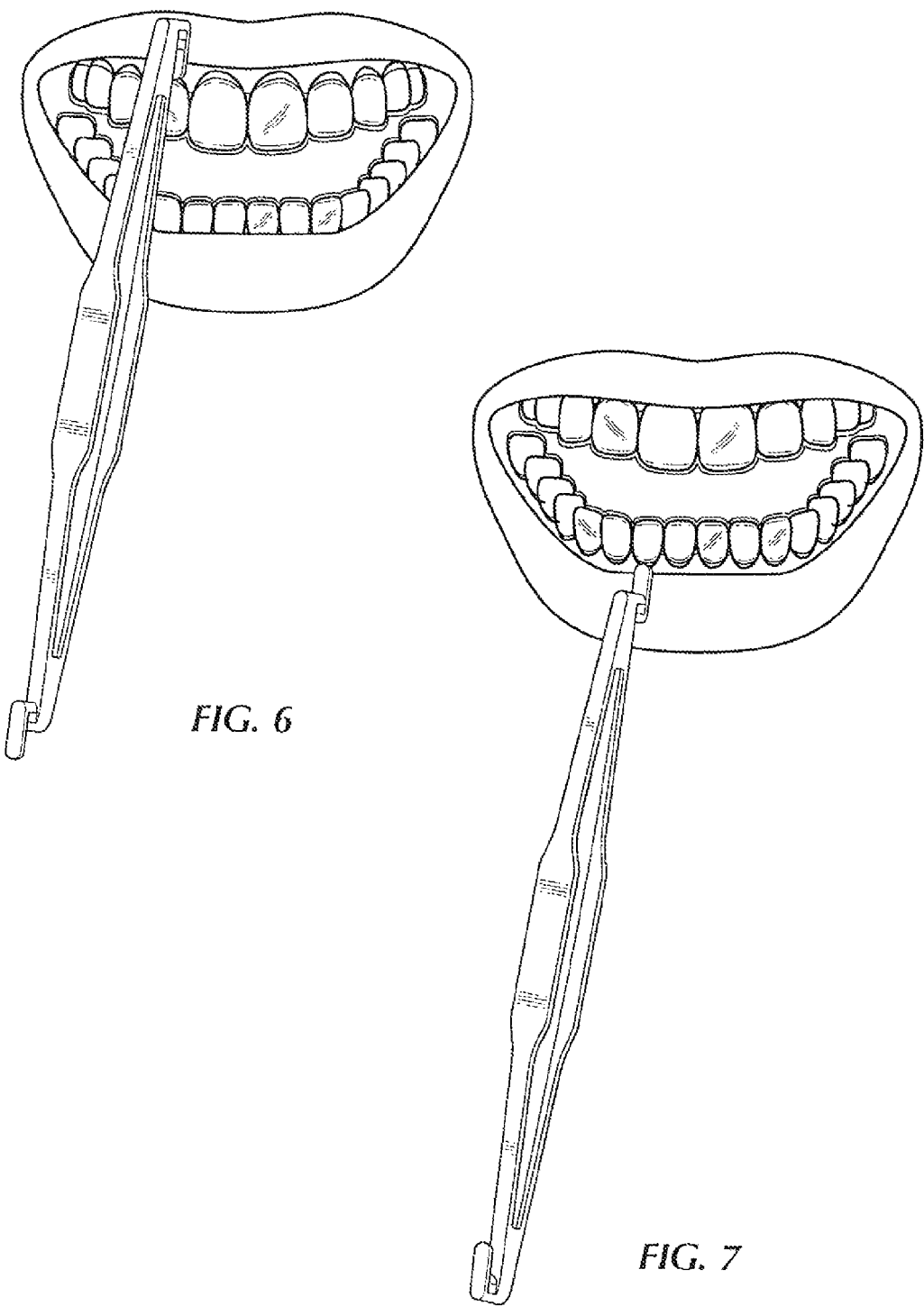
FIG. 6: Photo illustration. Using the Hook appendage to pull off upper aligner
FIG. 7: Photo illustration. Using the Lever appendage to push off bottom aligner

Referring now to FIG. 6 the OUTIE TOOL is illustrated in a position to engage and remove upper appliance using the hook appendage to pull off the aligner/appliance. The hook is inserted under the appliance and in between the patient's teeth sliding carefully to a place typically in between the teeth to easily slide under. By the application of downward force, the upper aligner is dislodged and removed from the teeth of the patient in a safe and effective manner.

Referring now to FIG. 7 the OUTIE TOOL is illustrated in a position to engage and remove lower appliance using the lever appendage to push off bottom aligner/appliance. The lever is inserted in under the appliance and between the person's teeth sliding carefully to a place typically in between the teeth to easily slide under. By the application of upward force, the lower aligner is dislodged and removed from the teeth of the patient in a safe and effective manner.

As shown in figures and with particular reference to FIG. 1, the present device includes an elongated barrel portion 12 defining a longitudinal dimension. A flat hook appendage 14 is on a distal end segment 16 of the barrel portion 12. The hook appendage 14 includes a transverse segment 18 extending transversely away from the barrel portion in the first transverse direction relative to the longitudinal dimension as shown. The transverse segment 18 of the hook appendage has a first end coupled to the barrel portion 12 and a second end coupled to a leg potion 20, which extends in the longitudinal dimension toward a proximal end segment 22 of the barrel potion 12 such that the hook appendage 14 and distal end segment 16 of the barrel portion 12 form a generally U-shaped structure.

FIG. 1 also shows that a flat lever appendage 24 is on the proximal end segment 22 of the barrel portion 12. The lever appendage 24 includes a transverse segment 26 extending transversely away from the barrel portion 12 in a second transverse direction relative to the longitudinal dimension, and as shown in FIG. 1 the second transverse direction is generally opposite the first transverse direction along which the transverse segment 18 of the hook appendage 14 extends. The transverse segment 26 of the lever appendage 24 has a first end coupled to the barrel portion 12 and a second end coupled to a leg portion 28, which extends in the longitudinal dimension away from the proximal end segment 22 of the barrel portion 12 such that the lever appendage 24 and proximal end segment 22 of the barrel portion 12 form a generally L-shaped structure. If desired, a central segment 30 of the barrel portion 12 may be thicker than the proximal and distal end segments 22, 16.

With this structure, a patient can use the device of FIG. 1 to remove a tooth positioning appliance on a tooth of the patient by positioning the hook appendage 14 above the tooth positioning appliance on the upper gum line between the upper teeth of the patient. The patient insets the hook appendage 14 between the tooth positioning appliance and the teeth of the patient and exerts a force downward thereby causing the tooth positioning to release from the upper teeth of the patient. Furthermore, the patent can position the lever appendage 22 below a tooth positioning appliance on a lower gum line between the teeth of the patient, insert the lever appendage between the tooth positioning appliance and the teeth of the patient, and exert a force upward thereby causing the tooth positioning to release from the lower teeth of the patient. The force exerted to the handle portion can be in a direction substantially parallel to the teeth of the patient.

I claim:

1. A dental apparatus comprising:
an elongated barrel portion defining a longitudinal direction;
a hook appendage on a distal end segment of the barrel portion, the hook appendage including only a straight transverse segment and a straight leg portion, the straight transverse segment extending transversely away from the barrel portion in a first transverse direction relative to the longitudinal direction, the straight transverse segment of the hook appendage having a first end coupled to the barrel portion and a second end, the second end being coupled to the straight leg portion, the straight leg portion extending in the longitudinal direction toward a proximal end segment of the barrel portion such that the hook appendage and distal end segment of the barrel portion form a generally U-shaped structure, both the distal and proximal end segments of the barrel portion defining straight structures without bends or appendages other than the hook appendage and a lever appendage; and
the lever appendage being on the proximal end segment of the barrel portion, the lever appendage being the only structure on the proximal end segment of the barrel portion and being defined by a transverse segment extending transversely away from the barrel portion in a second transverse direction relative to the longitudinal direction, the second transverse direction being generally opposite the first transverse direction, the transverse segment of the lever appendage having a first end coupled to the barrel portion and a second end, the second end being coupled to a leg portion extending in the longitudinal direction away from the proximal end segment of the barrel portion such that the lever appendage and proximal end segment of the barrel portion form a generally L-shaped structure and such that no U-shaped structure is formed on the proximal end segment of the barrel portion, the dental apparatus configured for removing dental appliances from a patient's teeth or tooth.

2. The apparatus of claim 1 wherein the apparatus is constructed of a unitary piece of axially rigid plastic.

3. The apparatus of claim 1 wherein both appendages of the apparatus are thin, flat, non-tapered so as to engage fully in between the appliance and the teeth of the patient.

4. The apparatus of claim 1, wherein a central segment of the barrel portion is thicker than the proximal and distal end segments.

5. A method for enabling a patient to remove a tooth positioning appliance on a tooth of the patient, comprising:

positioning a U-shaped hook appendage of a removal device having an elongated body on opposite ends of which are only the hook appendage and an L-shaped lever appendage and no other bends or appendages above the tooth positioning appliance on an upper gum line between upper teeth of the patient, the hook appendage including a portion of the body, a straight transverse segment, and a straight leg portion;

inserting the hook appendage between the tooth positioning appliance and the teeth of the patient;

exerting force downward thereby causing the tooth positioning to release from the upper teeth of the patient;

positioning the lever appendage below a tooth positioning appliance on a lower gum line between the teeth of the patient;

inserting the lever appendage between the tooth positioning appliance and the teeth of the patient; and exerting a pushing force upward thereby causing the tooth positioning appliance to release from the lower teeth of the patient.

6. The method of claim 5, wherein force exerted to the handle portion is in a direction substantially parallel to the teeth of the patient.

7. A dental apparatus comprising:

an elongated barrel portion defining a longitudinal direction, a first transverse direction perpendicular to the longitudinal direction, and a second transverse direction opposite the first transverse direction;

a hook appendage on a distal end segment of the barrel portion in the first transverse direction, the hook appendage including a straight transverse segment extending transversely away from the barrel portion, the straight transverse segment of the hook appendage having a first end coupled to the barrel portion and a second end, the second end being coupled to a straight leg portion extending in the longitudinal direction toward a proximal end segment of the barrel portion, the dental apparatus having no other structure on the distal end segment apart from the hook appendage; and a lever appendage on the proximal end segment of the barrel portion in the second transverse direction, the lever appendage including a transverse segment extending transversely away from the barrel portion, the transverse segment of the lever appendage having a first end coupled to the barrel portion and a second end, the second end being coupled to a leg portion extending in the longitudinal direction away from the proximal end segment of the barrel portion.

8. The apparatus of claim 7, wherein the transverse segment of the hook appendage extends from the barrel portion in a first transverse direction relative to the longitudinal direction and the transverse segment of the lever appendage extends from the barrel portion in a second transverse direction relative to the longitudinal direction, the second transverse direction being generally opposite the first transverse direction.

9. The apparatus of claim 7, wherein the hook appendage and distal end segment of the barrel portion form a generally U-shaped structure.

10. The apparatus of claim 7, wherein the lever appendage and proximal end segment of the barrel portion form a generally L-shaped structure.

11. The apparatus of claim 7, wherein a central segment of the barrel portion is thicker than the proximal and distal end segments.

* * * * *